United States Patent [19]

Omura et al.

[11] Patent Number: 4,594,338
[45] Date of Patent: Jun. 10, 1986

[54] THIOETHER DERIVATIVES OF TYLOSIN

[76] Inventors: Satoshi Omura, 12-7 Seta 5-Chome, Setagaya-ku, Tokyo; Kazuo Tsuzuki, 18-22, Nishi-Azabu 4-Chome, Minato-ku, Tokyo, both of Japan

[21] Appl. No.: 702,533

[22] Filed: Feb. 19, 1985

[30] Foreign Application Priority Data

Feb. 27, 1984 [GB] United Kingdom ............... 8405087

[51] Int. Cl.$^4$ .................... A61K 31/70; C07H 17/08
[52] U.S. Cl. .................................. 514/30; 536/7.1
[58] Field of Search ......................... 536/7.1; 514/30

[56] References Cited

U.S. PATENT DOCUMENTS

| | | | |
|---|---|---|---|
| 4,196,280 | 4/1980 | Umezawa et al. | 536/17 R |
| 4,366,309 | 12/1982 | Ganguly et al. | 536/7.1 |
| 4,443,436 | 4/1984 | Kirst et al. | 424/180 |
| 4,454,314 | 6/1984 | Nagel | 536/7.1 |
| 4,515,941 | 5/1985 | Fujiwara et al. | 536/7.1 |

OTHER PUBLICATIONS

Rossoff, "Handbook of Veterinary Drugs", Springer Publishing Co., N.Y., N.Y., 1974, pp. 628–629.
Tanaka, et al., "Synthesis of 9-Substituted Josamicin, 13-Substituted Isojosamycin and Their Tetrahydro Derivatives," *J. Antibiotics* 34(9), 1137–1151 (1981).
Omoto et al., "Modification of the Macrolide Antibiotic Midecamycin III, Formation of Neoisomidecamycin," *J. Antibiotics* 35(11), 1521–1526 (1982).
Fukagawa et al., "Deepoxidation of 16-Membered Epoxyenone Macrolide Antibiotics," *J. Antibiotics* 37(2), 108–135 (1984).
Derwent Abstract 85-071701/12 (Toyo Jozo) Abstracting Japanese Patent J6 0026-000-A published Feb. 8, 1985.

*Primary Examiner*—Johnnie R. Brown
*Attorney, Agent, or Firm*—Nancy J. Harrison; Arthur R. Whale

[57] ABSTRACT

11-Thioether and certain C-20 acetal and thioacetal derivatives of tylosin and demycarosyltylosin are effective antibacterial agents. Processes for preparing, formulations containing, and methods of treating bacterial infections with these derivatives are provided.

12 Claims, No Drawings

THIOETHER DERIVATIVES OF TYLOSIN

SUMMARY OF THE INVENTION

This invention relates to macrolide antibiotics, in particular to compounds similar to the well-known macrolide antibiotic tylosin (see, for example *Tetrahedron Letters*, 2339 (1970) and U.S. Pat. No. 3,178,341).

Despite tylosin's great value, there exists a constant and continuing need to develop new antibiotics of this type, both in view of the possibility of emergence of resistant strains, and with a view to improvement in the quantum and/or spectrum of antibiotic activity.

Numerous attempts have been made to modify the tylosin nucleus so as to produce new antibiotics of value, see for instance U.S. Pat. Nos. 4,321,361 and 4,334,019, but thus far none of those modified tylosin derivatives have reached the market place.

According to the present invention there is provided a compound of formula (I):

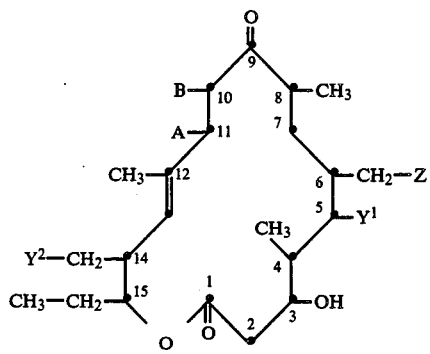

wherein A represents a group of formula —SR$^1$ where R$^1$ is a C$_{1-6}$ alkyl or C$_{2-6}$ hydroxyalkyl group or a monovalent aryl group when B represents a hydrogen atom;

or A and B taken together represent a single chemical bond;

wherein Y$^1$ represents a group of formula:

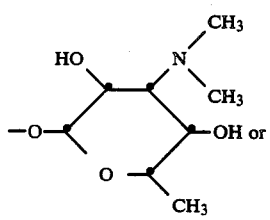

wherein Y$^2$ represents a group of formula:

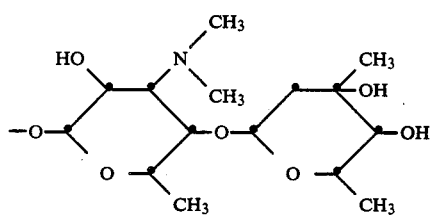

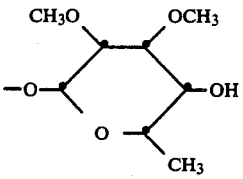

and Z represents CHO or a group of formula

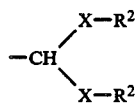

where X represents an oxygen or sulfur atom and R$^2$ is C$_{1-3}$ alkyl or aryl;

provided that, when A and B taken together represent a single chemical bond, then Z cannot be —CHO and X cannot be oxygen;

or a pharmacologically-acceptable salt thereof.

The formula (I) compounds are useful antibacterial agents. Thus, formulations comprising, and methods of treating bacterial infections in animals with, the formula (I) compounds and their pharmacologically acceptable salts are also part of this invention.

In another aspect, this invention provides a process for preparing a compound of formula (I) which comprises:

(a) reacting tylosin or demycarosyltylosin with a compound of formula R$^2$OH, R$^2$SH or (R$^2$)$_2$S so as to form an acetal or thioacetal of formula (I) in which Z represents:

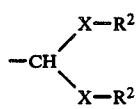

and A and B taken together represents a single chemical bond and/or;

(b) reacting a compound of formula (I) in which Z represents:

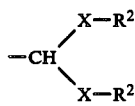

and A and B taken together represent a single bond, with a thiol of formula R$^1$SH so as to form a compound of formula I in which A represents SR$^1$ and B is hydrogen;

(c) hydrolysing a compound of formula (I) in which Z represents:

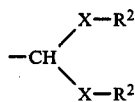

A represents SR$^1$ and B is hydrogen, so as to prepare a compound of formula (I) in which Z is —CHO, A is SR$^1$ and B is hydrogen; and (d) optionally salifying any compound of formula I produced above so as to form the corresponding pharmacologically-acceptable salt.

DETAILED DESCRIPTION OF THE INVENTION

This invention provides new thioether macrolide derivatives of formula (I) and their pharmacologically acceptable salts.

Although no stereochemical configuration is indicated in the above structural formula, it is to be understood that the stereochemistry is identical to that of tylosin. The $Y^2$ sugar is mycinose and the $Y^1$ sugars are mycaminose and mycarose.

The term "$C_{1-6}$ alkyl group" as used herein includes both straight and branched alkyl groups, for example, methyl, ethyl, propyl, isopropyl, n-butyl, t-butyl, pentyl and hexyl. The term "$C_{2-6}$ hydroxyalkyl" includes groups such as hydroxyethyl, hydroxypropyl and hydroxybutyl.

The term "aryl group" as used herein refers to a monovalent aromatic hydrocarbon group, preferably, to an optionally substituted phenyl group. The aryl, preferably phenyl, group may be substituted by a halogen atom such as chlorine or bromine, an amino group, a $C_{1-4}$ alkyl group such as methyl, ethyl, propyl, n-butyl or t-butyl, or a $C_{1-4}$ alkoxy group such as methoxy, ethoxy, propoxy, n-butoxy or t-butoxy. Such substituted aryl groups may include for instance, halophenyl groups, such as chlorophenyl or bromophenyl; $C_{1-4}$ alkylphenyl groups such as tolyl, xylyl, ethylphenyl or butylphenyl; or $C_{1-4}$ alkoxyphenyl groups, such as methoxyphenyl, ethoxyphenyl, propoxyphenyl, n-butoxyphenyl or t-butoxyphenyl. The preferred $R^2$ aryl group is phenyl.

The term "$C_{1-3}$ alkyl group" as used herein means methyl, ethyl, n-propyl or i-propyl.

Preferred compounds of the invention are those wherein Z is —CHO and A is —$SR^1$ where $R^1$ is an optionally substituted phenyl group.

The compounds of formula (I) can be prepared by reacting tylosin or demycarosyltylosin with a compound of formula $R^2OH$, $R^2SH$ or $(R^2)_2S$, where $R^2$ is as defined above, to form a compound of formula (IA):

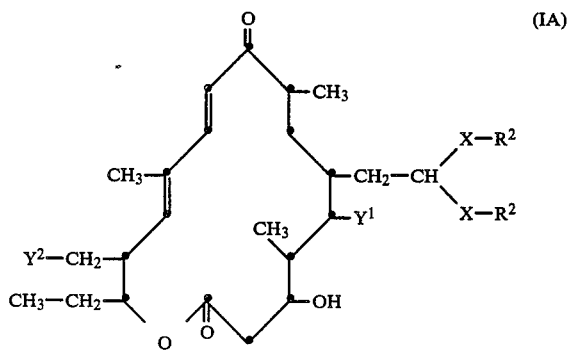

In this reaction, when X represents oxygen, it is preferred that $R^2$ be alkyl, when X represents sulfur, it is preferred that $R^2$ be aryl.

Compounds of formula (I) in which A represents —$SR^1$ and B represents hydrogen, and Z is an acetal or thioacetal group, can be prepared by reacting the compound of formula (IA) with a thiol of formula:

$R^1$—SH where $R^1$ is as previously defined. This thioetherification can be carried out using Michael-type conditions.

The acetal or thioacetal group:

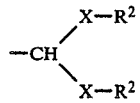

can then be transformed by hydrolysis to yield compounds of formula (I) in which Z is —CHO. If necessary, hydrolysis products of formula (I) can be converted to the corresponding pharmacologically acceptable salt by conventional means.

The tylosin acetal of formula (I) in which X is an oxygen atom and $Y^1$ is mycarosylmycaminosyl may be prepared by reacting tylosin with a hydroxy derivative of formula $R^2OH$ such as an alkanol or a phenol. The alkanol may be methanol, ethanol or propanol. The phenol may be, for instance, phenol, a halogen-substituted phenol such as chlorophenol or bromophenol, a $C_{1-4}$ alkyl-substituted phenol such as cresol, xylenol or ethylphenol or a $C_{1-4}$ alkoxy-substituted phenol such as methoxyphenol or ethoxyphenol. The acetalization may be carried out by using the alkanol to be acetalized in excess as the solvent. As other solvents there may be used benzene, acetonitrile, a chlorinated hydrocarbon such as chloroform, or an ether such as tetrahydrofuran.

The demycarosyltylosin acetal of formula I in which X is an oxygen atom and $Y^1$ is a mycaminosyl group, may be prepared by reacting demycarosyltylosin under substantially the same conditions as used for the preparation of the tylosin acetal. The demycarosyltylosin acetal also may be prepared directly from tylosin by acetalization, if the acetalization is carried out under anhydrous conditions using a mineral acid. In such a circumstance, simultaneous acetalization of the C-20 aldehyde group will occur with simultaneous cleavage of the mycarosyl sugar from the C-5 moiety. As examples of mineral acids suitable for use in this reaction there may be mentioned hydrochloric acid and sulfuric acid. Concentrations of the mineral acid may appropriately range from about 0.2 to 1%. In order to adjust the acid concentration, acidic methanol, typically hydrogen chloride in methanol, may be used.

The demycarosyltylosin thioacetals represented by the general formula I in which X is a sulfur atom may be prepared by reacting tylosin or demycarosyltylosin with a thiol of formula $R^2SH$ or a disulfide $(R^2)_2S$. The thiol to be used may be a $C_{1-3}$ alkanethiol or an arylthiol. Examples of $C_{1-3}$ alkanethiols are methanethiol, ethanethiol and propanethiol. The arylthiol may be thiophenol, a halogen-substituted thiophenol such as chlorothiophenol, or bromothiophenol, a $C_{1-4}$ alkyl-substituted thiophenol such as thiocresol, xylenethiol, ethylthiophenol, propylthiophenol or isopropylthiophenol or a $C_{1-4}$ alkoxy-substituted thiophenol such as methoxythiophenol, ethoxythiophenol or propoxythiophenol. The disulfide may be a $C_{1-3}$ alkyl disulfide or an aryl disulfide. As examples of the alkyl disulfide there may be mentioned methyl disulfide, ethyl disulfide or propyl disulfide. As the aryl disulfide there may be mentioned phenyl disulfide or a substituted phenyl disulfide such as tolyl disulfide or methoxyphenyl disulfide.

The thioacetalization may be carried out in the presence of a phosphine such as a tertiary phosphine using a suitable solvent. The phosphine to be used may be a tri-$C_{1-4}$-alkylphosphine such as trimethylphosphine, triethylphosphine or tributylphosphine or a triarylphosphine such as triphenylphosphine. Tri-n-butylphosphine is the preferred reagent. The solvent to be used may be benzene, acetonitrile or a chlorinated hydrocarbon such as chloroform. The thioacetalization may be effected at temperatures from 0° C. to the reflux temperature of the solvent, for periods ranging from about 15 minutes to 24 hours.

As indicated above, macrolide derivatives of formula IB:

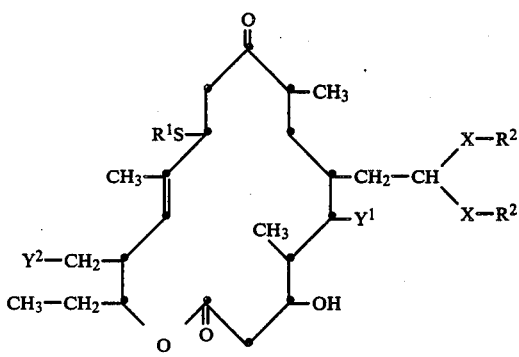

may be prepared by reacting a tylosin acetal or thioacetal or demycarosyltylosin acetal or thioacetal of formula (IA) with a thiol of formula $R^1SH$. The thiol to be used may be an alkanethiol or an arylthiol. The alkanethiol may be a $C_{1-6}$ alkanethiol such as methanethiol, ethanethiol, n-propanethiol, isopropanethiol, n-butanethiol, tert.-butanethiol, n-pentanethiol or n-hexanethiol. The arylthiol may be thiophenol, a halothiophenol such as chlorothiophenol or bromothiophenol, an aminothiophenol such as 4-aminothiophenol, a $C_{1-4}$ alkyl-substituted thiophenol such as thiocresol, xylenethiol, ethylthiophenol, propylthiophenol or a $C_{1-4}$ alkoxy-substituted thiophenol such as methoxythiophenol, ethoxythiophenol or propoxythiophenol.

The thioetherification is preferably effected in the presence of a base using an appropriate solvent. The base to be used may be, for instance, an aliphatic tertiary amine such as triethylamine, a nitrogen-containing heterocyclic compound such as pyridine, an alkali metal alkoxide such as sodium methoxide, sodium ethoxide, sodium propoxide, potassium methoxide, potassium ethoxide, lithium methoxide or lithium ethoxide, or sodium hydride. A base such as pyridine may also be used as the solvent. As other solvents there may be mentioned chlorinated hydrocarbons such as chloroform, and alkanols such as methanol or ethanol. This thioetherification reaction is preferably conducted under a nitrogen atmosphere at the reflux temperature of the solvent to be used. The reaction time may range from 1 to 24 hours.

The macrolide derivatives of formula (IC):

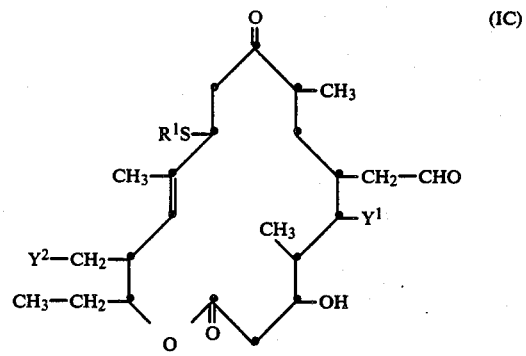

may be prepared by cleaving the acetal or thioacetal group from C-20 by hydrolysis.

For compounds of formula (I) in which $Y^1$ is mycaminosyloxy, the hydrolysis may be accomplished using a mineral acid such as hydrochloric acid and using as solvent a water-miscible compound such as an alkanol, for example, methanol or ethanol, acetonitrile or an ether such as tetrahydrofuran. The reaction temperature may range from 0° C. to the reflux temperature of the solvent, and the reaction time may range from about 30 minutes to 24 hours.

However, for the hydrolysis of compounds of formula (IC) in which $Y^1$ is mycarosyloxymycaminosyloxy, there is a risk that the mycarosyl group will be cleaved during the hydrolysis reaction. Accordingly, if it is desired to retain the mycarosyl group, mild hydrolysis conditions should be used. In this case, the hydrolysis may be appropriately carried out using an ether such as tetrahydrofuran or acetonitrile as the solvent at temperatures from about 0° C. to 60° C. for reaction periods ranging from about 30 minutes to 24 hours.

The diphenyl thioacetal derivatives are preferably hydrolyzed with mercury(II) oxide and boron trifluoride etherate in aqueous tetrahydrofuran under a nitrogen atmosphere.

According to one aspect of the invention there is provided a process for preparing a compound of formula (I) which comprises:

(a) reacting tylosin or demycarosyltylosin with a compound of formula $R^2OH$, $R^2SH$ or $(R^2)_2S$ so as to form an acetal or thioacetal of formula (I) in which Z represents:

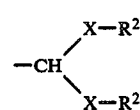

and A and B taken together represents a single chemical bond and/or;

(b) reacting a compound of formula (I) in which Z represents:

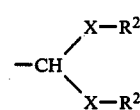

and A and B taken together represent a single bond, with a thiol of formula $R^1SH$ so as to form a compound of formula I in which A represents SR¹ and B is hydrogen; and/or (c) hydrolysing a compound of formula (I) in which Z represents:

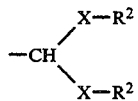

A represents SR¹ and B is hydrogen, so as to prepare a compound of formula (I) in which Z is —CHO, A is SR¹ and B is hydrogen; and (d) optionally salifying any compound of formula I produced above so as to form the corresponding pharmacologically-acceptable salt.

Examples of pharmacologically-acceptable salts are acid-addition salts with an organic acid, e.g., tartaric acid, acetic acid, propionic acid, lactic acid, citric acid or succinic acid or an inorganic acid, e.g., hydrochloric acid, sulfuric acid or phosphoric acid. The pharmacologically acceptable salts may be prepared in conventional manner, for instance, by dissolving the compound of formula (I) in the form of a base and the relevant acid in a mixture of solvents, agitating the mixture and, if necessary, cooling to form the corresponding acid addition salt.

The compounds of formula (I) and their pharmacologically acceptable salts possess good antibacterial activity, particularly against gram-positive bacteria and, macrolide-resistant strains. Accordingly, this invention also relates to a method for treating (which includes preventing) bacterial infections in animals, including warm-blooded mammals, which comprises administering an effective amount of a formula (I) compound or a pharmacologically acceptable salt thereof to the animal.

In another aspect, the invention provides a veterinary or pharmaceutical formulation which comprises as an active ingredient a compound of formula (I), or a pharmacologically-acceptable salt thereof, together with one or more excipients or carriers therefor.

The antibacterial formulation according to the present invention may be administered in the form of a solid preparation such as a capsule, tablet or granule or in a liquid preparation such as a solution or suspension, orally or rectally, or parenterally such as via an injection. These preparations may contain conventional excipients or carriers such as binders, suspending agents, emulsifying agents, buffers, etc.

Dosages which are effective for treating bacterial infections will vary with the activity of the active ingredient and the therapeutic indication. In general, however, typical dosages will range from 1 mg/kg to 100 mg/kg when administered as a pharmaceutical, and from 1 mg/kg to 1,000 mg/kg when administered as a veterinary.

The present invention will be described in more detail with reference to the following non-limiting Examples. In these Examples NMR spectrum refers to nuclear-magnetic resonance spectrum and EI-mass spectrum refers to electron-impact mass spectrum.

PREPARATION 1

Tylosin Dimethyl Acetal (Compound A)

To a solution of 1 gram of tylosin in 20 ml of methanol was added 0.34 ml of difluoroacetic acid, and the mixture was allowed to stand at room temperature for 2 days. After the completion of the reaction, the reaction mixture was neutralized with sodium hydrogen carbonate and then methanol was distilled off under reduced pressure to leave residues which in turn were mixed with 50 ml of water. The product was then extracted with three 50 ml portions of ethyl acetate and the resulting extract was dried over sodium sulfate. Concentration of the dried extract under reduced pressure yielded 800 mg of the crude title product as a pale yellow solid, which was purified by silica gel column chromatography using a chloroform/methanol (10/1) mixture to yield 400 mg of pure tylosin dimethyl acetal (Compound A).

Proton NMR spectrum (CDCl₃)δ3.25, 3.30 (each 3H, s, C-20 (OCH₃)₂).

EI-Mass spectrum: M+ (m/z) 961.

PREPARATION 2

Demycarosyltylosin Dimethyl Acetal (Compound B)

A solution of 10 grams of tylosin in 100 ml of a 0.5% hydrogen chloride-methanol mixture was allowed to react at room temperature for 1 hour. After the completion of the reaction, the reaction mixture was poured into a saturated sodium hydrogen carbonate aqueous solution and then extracted with chloroform. The resulting chloroform layer was dried over anhydrous sodium sulfate and concentrated under reduced pressure to dryness to give crude title product in solid form. This material was purified by silica gel column chromatography using a chloroform:methanol:concentrated ammonia (50:1:0.05) mixture to yield 8.5 grams (95% yield) of demycarosyltylosin dimethyl acetal (Compound B).

EI-Mass spectrum (m/z): 817 (M+), 468 (aglycone), 190, 174 (mycaminose).

Proton NMR spectrum δ(ppm): 1.69 (3H, 2, $H_{22}$), 2.49 (6H, s, N(CH₃)₂), 3.23, 3.28 (each 3H, s, acetal OCH₃), 3.45, 3.58 (each 3H, s, 2″-OCH₃, 3″-OCH₃), 4.30 (1H, d, J=7.5 Hz, $H_{1'}$), 4.55 (1H, d, J=7.5 Hz, $H_{1''}$), 4.96 (1H, bt, $J_{15,16}$=7.5 Hz, $H_{15}$), 5.86 (1H, bd, J=11.0 Hz, $H_{13}$), 6.25 (1H, d, J=15.0 Hz $H_{10}$), 7.28 (1H, d, J=15.0 Hz, $H_{11}$).

EXAMPLE 1

Tylosin Diphenyl Thioacetal (Compound C)

To a solution of 10 grams of tylosin and 3.6 grams of phenyl disulfide in 80 ml of chloroform were added 4.5 ml of tri-n-butylphosphine under a nitrogen atmosphere. The mixture was allowed to react at room temperature for 2 hours. After completion of the reaction, the resulting reaction mixture was concentrated under reduced pressure and purified by means of silica gel column chromatography using a chloroform/methanol/conc. ammonia (50/1/0.05) eluent to yield 7.9 of tylosin diphenyl thioacetal (Compound C).

EI-Mass spectrum (m/z): 1117 (M+), 608 (aglycone), 318 (mycarosylmycaminose), 191 (mycinose).

Proton NMR spectrum, δ(ppm): 1.77 (3H, s, $H_{22}$), 2.57 (6H, s, N(CH₃)₂), 3.45, 3.59 (each 3H, s, 2‴-OCH₃, 3‴-OCH₃), 4.16 (1H, d, J=7.5 Hz, $H_{1'}$), 4.54 (1H, d, J=8.0 Hz, $H_{1'''}$), 5.0(1H, b, $H_{15}$), 5.06 (1H, b, $H_{1''}$), 5.83 (1H, d, J=9.5 Hz, $H_{13}$), 6.23 (1H, d, J=13.5 Hz, $H_{10}$), 7.1–7.6 (m, $H_{11}$, aromatic ring proton).

EXAMPLE 2

10, 11-Dihydro-11-(phenylthio)tylosin Diphenyl Thioacetal (Compound D)

A solution of 1.0 gram of tylosin diphenyl thioacetal (Compound C) and 1.0 ml of thiophenol in 20 ml of triethylamine was refluxed for 4 hours under a nitrogen atmosphere. After completion of the reaction, the resulting reaction mixture was concentrated under reduced pressure and purified by means of silica gel column chromatography using a chloroform/methanol/conc. ammonia (40/1/0.05) mixture to yield 438 mg (40%) of 10, 11-dihydro-11-phenylthiotylosin diphenylthio acetal (Compound D).

EI-Mass spectrum (m/z): 718, 702(aglycone), 191 (mycinose), 174 (mycaminose).

Proton NMR spectrum, $\delta$(ppm): 1.63 (3H, s, $H_{22}$), 2.46 (6H, s, $N(CH_3)_2$), 3.43, 3.56 (each 3H, s, $2'''$-$OCH_3$, $3'''$-$OCH_3$), 4.35 (1H, d, J=7.5 Hz, $H_{1'''}$), 4.67 (1H, bd, J=9.0 Hz, $H_{13}$), 4.8 (1H, b, $H_{15}$), 5.00 (1H, bd, 1H, $H_{1''}$), 7.2 (m, aromatic ring proton).

EXAMPLE 3

11-(p-Aminophenylthio)-10,11-dihydrotylosin Diphenyl Thioacetal (Compound E)

A solution of 100 mg of tylosin diphenyl thioacetal (Compound C) and 70 mg of p-aminothiophenol of triethylamine was refluxed for 5 hours under a nitrogen atmosphere. After the completion of the reaction, the resulting reaction mixture was concentrated under reduced pressure and purified by means of silica gel column chromatography using a chloroform/ methanol/conc. ammonia (15/1/0.05) mixture to yield mg (58%) of 11-(p-aminophenylthio)-10,11-dihydrotylosin diphenylthioacetal (Compound E).

EI-Mass spectrum (m/z): 717 (aglycone), 191 (mycinose), 174 (mycaminose).

Proton NMR spectrum, $\delta$(ppm): 1.66 (3H, s, $H_{22}$), 2.46 (6H, s, $N(CH_3)_2$), 3.48, 3.60 (each 3H, s, $2'''$-$OCH_3$, $3'''$-$OCH_3$), 4.44 (1H, d, J=8.0 Hz, $H_{1'''}$), 4.60 (1H, bd, J=9.0 Hz, $H_{13}$), 4.9 (b, $H_{15}$), 5.03 (1H, d, J=3.0 Hz, $H_{1''}$), 5.42, 6.95 (each 2H, d, J=8.0 Hz, —$SC_6H_4NH_2$), 7.3 (m, aromatic ring proton).

EXAMPLE 4

10,11-Dihydro-11-(p-Methylphenylthio)tylosin Diphenyl Thioacetal (Compound F)

A solution of 2.0 grams of tylosin diphenyl thioacetal (Compound C) and 2.3 grams of p-thiocresol in 40 ml of triethylamine was reacted under reflux for three hours. After completion of the reaction, the resulting reaction mixture was concentrated under reduced pressure and then purified by means of silica gel column chromatography using a chloroform/methanol/ conc. ammonia (50/1/0.05) mixture to give 860 mg (39%) of 10,11-dihydro-11-(p-methylphenylthio)tylosin diphenyl thioacetal (Compound F).

EI-Mass spectrum (m/z): 1241(M+), 1096(M+-mycarose), 191, 175 (mycinose), 174 (mycaminose), 161, 145 (mycarose).

Proton NMR spectrum, $\delta$(ppm): 1.63 (3H, s, $H_{22}$), 2.25 (3H, s, —$SC_6H_4CH_3$), 2.45 (6H, s, $N(CH_3)_2$), 3.44, 3.57 (each 3H, d, $2'''$-$OCH_3$, $3'''$-$OCH_3$), 4.10 (1H, d, J=7.0 Hz, $H_{1'}$), 4.36 (1H, d, J=8.0 Hz, $H_{1'''}$), 4.63 (1H, bd, J=9.0 Hz, $H_{13}$), 4.8 (b, $H_{15}$), 5.00 (1H, d, J=3.0 Hz, $H_{1''}$), 6.9-7.5 (m, aromatic ring proton).

EXAMPLE 5

11-(p-Chlorophenylthio)-10,11-dihydrotylosin Diphenyl Thioacetal (Compound G)

A solution of 1.0 gram of tylosin diphenyl thioacetal (Compound C) and 1.3 grams of p-chlorothiophenol in 20 ml of triethylamine was reacted under reflux for 24 hours under a nitrogen atmosphere. After the completion of the reaction, the resulting reaction mixture was concentrated under reduced pressure and purified by means of silica gel column chromatography using a chloroform/methanol/conc. ammonia mixture (50/1/0.05) to yield 418 mg (37%) of 11-(p-chlorophenylthio)-10,11-dihydrotylosin diphenyl thioacetal (Compound G).

EI-Mass spectrum (m/z): 927 (aglycone +mycinose), 191, 175 (mycinose), 174 (mycaminose), 161 (mycarose).

Proton NMR spectrum, $\delta$(ppm): 1.63 (3H, s, $H_{22}$), 2.47 (6H, s, $N(CH_3)_2$), 3.46, 3.60 (each 3H, s, $2'''$-$OCH_3$, $3'''$-$OCH_3$), 4.10 (1H, d, J=7.0 Hz, $H_{1'}$), 4.40 (1H, d, J=7.5 Hz, $H_{1'''}$), 4.69 (1H, bd, J=9.0 Hz, $H_{13}$), 4.9 (b, $H_{15}$), 5.05 (1H, bd, J=3.0 Hz, $H_{1''}$), 7.0-7.4 (m, aromatic ring proton).

EXAMPLE 6

10,11-Dihydro-11-(p-Methoxyphenylthio)tylosin Diphenyl Thioacetal (Compound H)

A solution of 1.0 gram of tylosin diphenyl thioacetal (Compound C) and 1.5 ml of p-methoxythiophenol in 20 ml of triethylamine was reacted under reflux for 4 hours under a nitrogen atmosphere. After completion of the reaction, the resulting reaction mixture was concentrated under reduced pressure and purified by means of silica gel column chromatography using a chloroform/methanol/conc. ammonia mixture (40/1/0.05) to yield 416 mg (37%) of 10,11-dihydro-11-(p-methoxyphenylthio)tylosin diphenyl thioacetal (Compound H).

EI-Mass spectrum (m/z): 764 (aglycone), 191, 175 (mycinose), 174 (mycaminose), 161, 145 (mycarose).

Proton NMR spectrum, $\delta$(ppm): 1.64 (3H, s, $H_{22}$), 2.45 (6H, s, $N(CH_3)_2$), 3.44 3.56 (each 3H, s, $2'''$-$OCH_3$, $3'''$-$OCH_3$), 3.68 (3H, s, —$SC_6H_4OCH_3$), 4.09 (1H, d, J=7.0 Hz, $H_{1'}$), 4.38 (1H, d, J=7.5 Hz, $H_{1'''}$), 4.56 (1H, bd, J=9.0 Hz, $H_{13}$), 4.8 (b, $H_{15}$), 5.00 (1H, d, J=3.0 Hz, $H_{1''}$), 6.5-7.4 (m, aromatic ring proton).

EXAMPLE 7

11-Ethylthio-10,11-dihydrotylosin Diphenyl Thioacetal (Compound I)

A solution of 200 mg of tylosin diphenyl thioacetal (Compound C) and 0.2 ml of ethanethiol in 4 of triethylamine was reacted under reflux for 4.5 hours under a nitrogen atmosphere. After completion of the reaction, the resulting reaction mixture was concentrated under reduced pressure and then purified by means of silica gel column chromatography using a chloroform/methanol/conc. ammonia mixture (15/1/0.05) to yield 150 mg (71%) of 11-ethylthio-10,11-dihydrotylosin diphenyl thioacetal (Compound I).

EI-Mass spectrum (m/z): 845 (aglycone +mycinose), 654 (aglycone), 191 (mycinose), 145 (mycarose).

Proton NMR spectrum, $\delta$(ppm): 1.63 (3H, s, $H_{22}$), 2.49 (6H, s, $N(CH_3)_2$), 3.48, 3.57 (each 3H, s, $2'''$-$OCH_3$), 4.16 (1H, d, J=7.0 Hz, $H_{1'}$), 4.48 (1H, d, J=7.5 Hz, $H_{1'''}$), 5.0 (b, $H_{13}$, $H_{15}$, $H_{1''}$), 7.3 (m, aromatic ring proton).

EXAMPLE 8

11-(Ethylthio)-10,11-dihydrodemycarosyltylosin Dimethyl Acetal (Compound J)

A solution of 200 mg of demycarosyltylosin dimethyl acetal (Compound B) and 0.2 ml of ethanethiol in 4 ml of triethylamine was reacted under reflux for 5 hours under a nitrogen atmosphere. After completion of the reaction, the resulting reaction mixture was concentrated under reduced pressure and then purified by means of silica gel column chromatography using a chloroform/methanol/conc. ammonia mixture (20/1/0.05) to yield 182 mg (85%) of 11-(ethylthio)-10,11-dihydrodemycarosyltylosin dimethyl acetal (Compound J).

EI-Mass spectrum (m/z): 879 ($M^+$), 688 ($M^+$-mycinose), 174 (mycaminose).

Proton NMR spectrum, δ(ppm): 1.67 (3H, s, $H_{22}$), 2.50 (6H, s, N($CH_3$)$_2$), 3.27 (6H, s, acetal—$OCH_3$), 3.50, 3.59 (each 3H, s, 2''—$OCH_3$, 3'''—$OCH_3$), 4.33 (1H, d, J=7.0 Hz, $H_{1'}$), 4.53 (1H, d, J=7.5 Hz, $H_{1''}$), 5.1 (6, $H_{15}$), 5.20 (1H, bd, J=9.5 Hz, $H_{13}$).

EXAMPLE 9

10,11-Dihydro-11-(2-hydroxyethylthio)demycarosyltylosin Dimethyl Acetal (Compound K)

A solution of 100 mg of demycarosyltylosin dimethyl acetal and 0.1 ml of 2-mercaptoethanol in 2 ml of triethylamine was reacted under reflux for 6.5 hours under a nitrogen atmosphere. After the reaction was over, the resulting reaction mixture was concentrated under reduced pressure and then purified by means of silica gel column chromatography using a chloroform/methanol/conc. ammonia mixture (20/1/0.05) to yield 40 mg (37%) of 10,11-dihydro-11-(2-hydroxyethylthio)demycarosyltylosin dimethyl acetal (Compound K).

EI-Mass spectrum (m/z): 530 (aglycone), 174 (mycaminose).

Proton NMR spectrum, δ(ppm): 1.83 (3H, s, $H_{22}$), 2.59 (6H, s, N($CH_3$)$_2$), 3.25 (6H, s, acetal $OCH_3$), 3.47, 3.56 (each 3H, s, 2''—$OCH_3$, 3'''—$OCH_3$), 4.41 (1H, d, J=7.5 Hz, $H_{1'}$), 4.50 (1H, d, J=7.5 Hz, $H_{1''}$), 5.0(b, H15), 5.10 (1H, bd, J=8.5 Hz, $H_{13}$).

EXAMPLE 10

10,11-Dihydro-11-(phenylthio)demycarosyltylosin Dimethyl acetal (Compound L)

A solution of 100 mg of demycarosyltylosin dimethyl acetal (Compound B) and 0.15 ml of thiophenol of triethylamine was reacted under reflux for 7 hours under a nitrogen atmosphere. After the reaction was over, the resulting reaction mixture was concentrated under reduced pressure and then purified by means of silica gel column chromatography using a chloroform/ methanol/conc. ammonia mixture (15/1/0.05) to yield 42 mg (37%) of 10,11-dihydro-11-(phenylthio)-demycarosyltylosin dimethyl acetal (Compound L).

EI-Mass spectrum (m/z): 927($M^+$), 753 ($M^+$-mycaminose), 190, 174 (mycaminose).

Proton NMR spectrum, δ(ppm): 1.63 (3H, s, $H_{22}$), 2.49 (6H, s, N($CH_3$)$_2$), 3.23 (6H, s, acetal-$OCH_3$), 3.44, 3.56 (each 3H, s, 2''—$OCH_3$, 3'''—$OCH_3$), 4.31 (1H, d, J=7.0 Hz, $H_{1'}$), 4.40 (1H, d, J=8.0 Hz, $H_{1''}$) 4.9 (2H, b, $H_{13'}$ $H_{15'}$ $H_{1''}$), 7.3 (m, aromatic ring proton).

EXAMPLE 11

11-(p-Aminophenylthio)-10,11-dihydrodemycarosyltylosin Dimethyl Acetal (Compound M)

A solution of 100 mg of demycarosyltylosin dimethyl acetal (Compound B) and 150 mg of p-aminothiophenol in 2 ml of triethylamine was reacted under reflux for 4.5 hours under a nitrogen atmosphere. After the reaction was over, the resulting reaction mixture was concentrated under reduced pressure and then purified by means of silica gel column chromatography using a chloroform/methanol/conc. ammonia mixture (15/1/0.05) to yield 41 mg (36%) of 11-(p-aminophenylthio)-10,11-dihydrodemycarosyltylosin dimethyl acetal (Compound M).

EI-Mass spectrum (m/z): 768($M^+$-mycaminose), 190 (mycaminose), 175 (mycinose).

Proton NMR spectrum, δ(ppm): 1.69 (3H, s, $H_{22}$), 2.52 (6H, s, N($CH_3$)$_2$), 3.26 (6H, s, acetal-$OCH_3$), 3.48, 3.59 (each 3H, s, 2''—$OCH_3$, 3'''—$OCH_3$), 4.31 (1H, d, J=8.0 Hz, $H_{1'}$), 4.45 (1H, d, J=8.0 Hz, $H_{1''}$), 4.77 (1H, bd, J=11.0 Hz, $H_{13}$), 4.92 (1H, bt, $J_{15,16}$=8.0 Hz, $H_{15}$), 6.56, 7.16 (each 2H, d, J=8.0 Hz, aromatic ring proton).

EXAMPLE 12

11-(Ethylthio)-10,11-dihydrodemycarosyltylosin (Compound N)

A solution of 120 mg of 11-(ethylthio)-10,11-dihydrodemycarosyltylosin dimethyl acetal (Compound J) in 1.5 ml of 0.1N HCl-acetonitrile (2.5:1) was reacted at room temperature for 1 hour. After the reaction was over, the resulting reaction mixture was poured into a saturated sodium bicarbonate aqueous solution and then extracted with chloroform. The chloroform layer was then dried over anhydrous sodium sulfate and concentrated to dryness under reduced pressure to give crude product purified by means of silica gel thin layer chromatography using a chloroform/methanol/conc. ammonia mixture (10/1/0.05) to yield 105 mg (92%) of 11-(ethylthio)-10,11-dihydrodemycarosyltylosin (Compound N).

$[\alpha]_D^{27}$: −14.9 (c 1, methanol).

uv: $\lambda_{max}^{MeOH}$nm(ε): 282 (2,7000).

EI-Mass spectrum (m/z): 833 ($M^+$), 642 ($M^+$-mycinose), 174 (mycaminose).

Proton NMR spectrum, δ(ppm): 1.67 (3H, s, $H_{22}$), 2.46 (6H, s, N($CH_3$)$_2$), 3.46, 3.55 (each 3H, s, 2''—$OCH_3$, 3'''—$OCH_3$), 4.26 (1H, d, J=8.0 Hz, $H_{1'}$), 4.48 (1H, d, J=8.0 Hz, $H_{1''}$), 5.0 (b, $H_{15}$), 5.17 (1H, bd, J=9.5 Hz, $H_{13}$), 9.66 (1H, s, $H_{20}$).

EXAMPLE 13

10,11-Dihydro-11-(2-hydroxyethylthio)demycarosyltylosin (Compound O)

A solution of 30 mg of 10,11-dihydro-11-(2-hydroxyethylthio)demycarosyltylosin edimethyl acetal (Compound K) in 1 ml of 0.1N HCl-acetonitrile (2.5:1) was reacted at room temperature for 1 hour. After the reaction was over, the resulting reaction mixture was treated in substantially the same manner as in Example 12 to yield 23 mg (81%) of 10,11-dihydro-11-(2-hydroxyethylthio)demycarosyltylosin (Compound O).

$[\alpha]_D^{27}$: −34.4° (c 0.5, methanol).

uv: $\lambda_{max}^{MeOH}$nm(ε): 285 (2,100).

EI-Mass spectrum (m/z): 468 (aglycone), 174 (mycaminose).

Proton NMR spectrum, δ(ppm): 1.81 (3H, s, H$_{22}$), 2.47 (6H, s, N(CH$_3$)$_2$), 3.46, 3.56 (each 3H, s, 2″—OCH$_3$, 3″—OCH$_3$), 4.33 (1H, s, J=7.5 Hz, H$_{1'}$), 4.50 (1H, s, J=7.5 Hz, H$_{1''}$), 5.08 (1H, bd, J=9.0 Hz, H$_{13}$), 5.1 (1H, b, H$_{15}$), 9.67 (1H, s, H$_{20}$).

EXAMPLE 14

11-(p-Aminophenylthio)-10,11-dihydrodemycarosyltylosin (Compound P)

A solution of 40 mg of 11-(p-aminophenylthio)-10,11-dihydrodemycarosyltylosin dimethyl acetal (Compound M) in 1 ml of 0.1N HCl-acetonitrile(2.5:1) was reacted at room temperature for 1 hour. After the reaction was over, the resulting reaction mixture was treated in substantially the same manner as in Example 12 to yield 32 mg (84%) of 11-(p-aminophenylthio)-10,11-dihydrodemycarosyltylosin (Compound P).

[α]$_D^{27}$: −18.3° (c 1, methanol).

uv: λ$_{max}^{MeOH}$nm(ε): 271 (13,000).

EI-Mass spectrum (m/z): 706(M+-mycaminose), 531 (aglycone), 191, 175 (mycinose), 190, 174 (mycaminose).

Proton NMR spectrum, δ(ppm): 1.69 (3H, s, H$_{22}$), 2.52 (6H, s, N(CH$_3$)$_2$), 3.48, 3.59 (each 3H, s, 2″—OCH$_3$, 3″—OCH$_3$), 4.31 (1H, d, J=8.0 Hz, H ), 4.45 (1H, d, J=8.0 Hz, H$_{1''}$), 4.77 (1H, bd, J=10.5 Hz, H$_{13}$), 4.92 (1H, bt, J$_{15,16}$=8.0 Hz, H$_{15}$), 6.56, 7.16 (each 2H, d, J=8.0 Hz, aromatic ring proton), 9.67(1H, s, H$_{20}$).

EXAMPLE 15

10,11-Dihydro-11-(phenylthio)demycarosyltylosin (Compound Q)

A solution of 40 mg of 10,11-dihydro-11-(phenylthio)demycarosyltylosin dimethyl acetal (Compound L) in 1 ml of 0.1N HCl-acetonitrile (2.5:1) was reacted at room temperature for 1 hour. After the reaction was over, the resulting reaction mixture was treated in substantially the same manner as in Example 12 to yield 25 mg (66%) of 10,11-dihydro-11-(phenylthio)demycarosyltylosin (Compound Q).

[α]$_D^{27}$: −11.4° (c 1, methanol).

uv: λ$_{max}^{MeOH}$nm(ε): 264 (4,700).

EI-Mass spectrum (m/z): 881(M+), 190, 174 (mycaminose).

Proton NMR spectrum, δ(ppm): 1.66 (3H, s, H$_{22}$), 2.47 (6H, s, N(CH$_3$)$_2$), 3,45, 3.54 (each 3H, s, 2″—OCH$_3$, 3″—OCH$_3$), 4.25 (1H, d, J=8.0 Hz, H$_{1'}$), 4.37 (1H, d, J=7.5 Hz, H$_{1''}$), 4.91 (1H, bd, J=9.0 Hz, H$_{13}$), 4.8-5.0(1H, b, H$_{15}$), 7.2-7.3 (m, aromatic ring proton), 9.66 (1H, s, H$_{20}$).

EXAMPLE 16

11-(Ethylthio)-10,11-dihydrotylosin (Compound R)

A solution of 150 mg of 11-(ethylthio)-10,11-dihydrotylosin diphenyl thioacetal (Compound I), 28 mg of mercury(II) oxide (red) and 0.02 ml of BF$_3$ etherate in 1.5 ml of 15% aqueous tetrahydrofuran was reacted at room temperature for 1 hour under a nitrogen atmosphere. After the reaction was over, the resulting reaction mixture was poured into a saturated sodium bicarbonate aqueous solution and extracted with diethyl ether. The resulting ether layer was dried over anhydrous sodium sulfate and concentrated under reduced pressure to dryness to give crude product which in turn was purified by means of silica gel thin layer chromatography using a chloroform/methanol/conc. ammonia mixture (12/1/0.05) to yield 37 mg (30%) of 11-(ethylthio)-10,11-dihydrotylosin (Compound R).

[α]$_D^{27}$: −50.0° (c 1, methanol).

uv: λ$_{max}^{MeOH}$nm(ε): 285 (7,100).

EI-Mass spectrum (m/z): 641 (aglycone+mycaminose), 484, 452 (aglycone), 175 (mycinose), 174 (mycaminose).

Proton NMR spectrum, δ(ppm): 1.64 (3H, s, H$_{22}$), 2.45 (6H, s, N(CH$_3$)$_2$), 3.47, 3.56 (each 3H, s, 2‴—OCH$_3$, 3‴—OCH$_3$), 4.50 (1H, d, J=8.0 Hz, H$_{1'}$), 4.52 (1H, d, J=8.0 Hz, H$_{1'''}$), 5.0 (3H, b, H$_{13}$, H$_{15}$, H$_{1''}$, 9.66 (1H, s, H$_{20}$).

EXAMPLE 17

10,11-Dihydro-11-(phenylthio)tylosin (Compound S)

A solution of 400 mg of 10,11-dihydro-11-(phenylthio)tylosin diphenyl thioacetal (Compound D), 310 mg of mercury(II) oxide (red) and 0.2 ml of BF$_3$ etherate in 4 ml of 15% aqueous tetrahydrofuran was reacted at room temperature for 1 hour under a nitrogen atmosphere. After the reaction was over, the resultant reaction mixture was treated in substantially the same manner as in Example 16 to yield 185 mg (55%) of 10,11-dihydro-11-(phenylthio)tylosin (Compound S).

[α]$_D^{27}$: −40.8° (c 1, methanol).

uv: λ$_{max}^{MeOH}$nm(ε): 262 (5,000).

EI-Mass spectrum (m/z): 864(M+-mycarose), 191 (mycinose), 174 (mycaminose).

Proton NMR spectrum, δ(ppm): 1.63 (3H, s, H$_{22}$), 2.47 (6H, s, N(CH$_3$)$_2$), 3.41, 3.54 (each 3H, s, 2‴−OCH$_3$, 3‴−OCH$_3$), 4.18 (1H, d, J=7.5 Hz, H$_{1'}$), 4.36 (1H, d, J=7.5 Hz, H$_{1'''}$), 4.84 (1H, d, J=9.5 Hz, H$_{13}$), 4.90.(1H, b, H$_{15}$), 4.99 (1H, bd, J=3.0 Hz, H$_{1'''}$), 7.2 (m, aromatic ring proton), 9.75 (1H, s, H$_{20}$).

EXAMPLE 18

11-(p-Chlorophenylthio)-10,11-dihydrotylosin (Compound T)

A solution of 300 mg of 11-(p-chlorophenylthio)-10,11-dihydrotylosin diphenyl thioacetal (Compound G), 30 mg of mercury(II) oxide (red) and 0.02 ml of BF$_3$ etherate in 3 ml of 15% aqueous tetrahydrofuran was reacted at room temperature for 1 hour under a nitrogen atmosphere. After the reaction was over, the resultant reaction mixture was treated in substantially the same manner as in Example 18 to yield 110 mg (44%) of 11-(p-chlorophenylthio)-10,11-dihydrotylosin (Compound T).

[α]$_D^{27}$: −53.6° (c 1, methanol).

uv: λ$_{max}^{MeOH}$nm(ε): 266 (8,500).

EI-Mass spectrum (m/z): 898 (M+-mycarose), 725 (aglycone+mycinose), 566 (aglycone), 191, 175 (mycinose), 174 (mycaminose).

Proton NMR spectrum, δ(ppm): 1.66 (3H, s, H$_{22}$), 2.52 (6H, s, N(CH$_3$)$_2$), 3.46, 3.59 (each 3H, s, 2''''—OCH$_3$, 3'''—OCH$_3$), 4.23 (1H, d, J=7.5 Hz, H$_{1'}$), 4.43 (1H, d, J=7.5 Hz, H$_{1'''}$), 4.62 (1H, bd, J=9.0 Hz, H$_{22}$), 4.9 (b, H$_{15}$), 5.04 (1H, d, J=3.0 Hz, H$_{1'''}$), 7.26 (s, aromatic ring proton)., 9.67 (1H, s, H$_{20}$).

EXAMPLE 19

11-(p-Aminophenylthio)-10,11-dihydrotylosin (Compound U)

A solution of 100 mg of 11-(p-aminophenylthio)-10,11-dihydrotylosin diphenyl thioacetal (Compound E), 110 mg of mercury(II) oxide (red) and 0.07 ml of BF3 etherate in 1 ml of 15% aqueous tetrahydrofuran was reacted at room temperature for 1 hour under a nitrogen atmosphere. After the reaction was over, the resultant reaction mixture was treated in substantially the same manner as in Example 16 to yield 15 mg (18%) of 11-(p-aminophenylthio)-10,11-dihydrotylosin (Compound U).

$[\alpha]_D^{27}$: $-59.6°$ (c 0.1, methanol).

uv: $\lambda_{max}^{MeOH}$nm($\epsilon$): 274 (16,000).

EI-Mass spectrum (m/z): 531 (aglycone), 191 (mycinose), 174 (mycaminose).

Proton NMR spectrum, $\delta$(ppm): 1.75 (3H, s, $H_{22}$), 2.53 (6H, s, $N(CH_3)_2$), 3.51, 3.60 (each 3H, s, $2'''$—$OCH_3$, $3'''$—$OCH_3$), 4.07 (1H, d, J=8.0 Hz, $H_{1'}$), 4.54 (1H, d, J=8.0 Hz, $H_{1'''}$), 5.1 (3H, b, $H_{1''}$, $H_{15}$, $H_{13}$), 6.55, 7.13 (each 2H, d, aromatic ring proton), 9.70 (1H, s, $H_{20}$).

EXAMPLE 20
10,11-Dihydro-11-(p-methylphenylthio)tylosin (Compound V)

A solution of 200 mg of 10,11-dihydro-11-(p-methylphenylthio)tylosin diphenyl thioacetal (Compound F), 140 mg of mercury(II) oxide (red) and 0.1 ml of BF3 etherate in 2 ml of 15% aqueous tetrahydrofuran was reacted at room temperature for 1 hour under a nitrogen atmosphere. After the reaction was over, the resultant reaction mixture was treated in substantially the same manner as in Example 18 to yield 47 mg (28%) of 10,11-dihydro-11-(p-methylphenylthio)tylosin (Compound V).

$[\alpha]_D^{27}$: $-46.0°$ (c 1, methanol).

uv: $\lambda_{max}^{MeOH}$nm($\epsilon$): 263 (6,700).

EI-Mass spectrum (m/z): 894($M^+$-mycarose), 706 (aglycone+mycinose), 318 (mycarosylmycaminose), 174 (mycaminose), 145 (mycarose).

Proton NMR spectrum, $\delta$(ppm): 1.66 (3H, s, $H_{22}$), 2.30 (3H, s, —$SC_6H_4CH_3$), 2.49 (6H, s, $N(CH_3)_2$), 3.46, 3.57 (each 3H, s, $2'''$—$OCH_3$, $3'''$—$OCH_3$), 4.43 (1H, d, J=8.0 Hz, J=3.0 Hz, $H_{1''}$), 7.03, 7.23 (each 2H, d, J=8.0 Hz, aromatic ring proton), 9.65 (1H, s, $H_{20}$).

EXAMPLE 21
10,11-Dihydro-11-(p-methoxyphenylthio)tylosin (Compound W)

A solution of 400 mg of 10,11-dihydro-11-(p-methoxyphenylthio)tylosin diphenyl thioacetal (Compound H), 70 mg of mercury(II) oxide (red) and 0.05 ml of BF3 etherate in 4 ml of 15% aqueous tetrahydrofuran was reacted at room temperature for 1 hour under a nitrogen atmosphere. After the reaction was over, the resultant reaction mixture was treated in substantially the same manner as in Example 16 to yield 170 mg (51%) of 10,11-dihydro-11-(p-methoxyphenylthio)tylosin (Compound W).

$[\alpha]_D^{27}$: $-49.7°$ (c 1, methanol).

uv: $\lambda_{max}^{MeOH}$nm($\epsilon$): 262 (5,400), 231 (10,200).

EI-Mass spectrum (m/z): 562, 530 (aglycone), 318 (mycarosylmycaminose), 174 (mycaminose).

Proton NMR spectrum, $\delta$(ppm): 1.69 (3H, s, $H_{22}$), 2.57 (6H, s, $N(CH_3)_2$), 3.47, 3.57 (each 3H, s, $2''''$—$OCH_3$, $3'''$—$OCH_3$), 3.76 (3H, s, —$SC_6H_4OCH_3$), 4.26 (1H, d, J=7.0 Hz, $H_{1'}$), 4.43 (1H, d, J=7.5 Hz, $H_{1'''}$), 4.78 (1H, bd, J=9.0 Hz, $H_{13}$), 4.9 (b, $H_{15}$), 5.05 (1H, d, J=3.0 Hz, $H_{1''}$), 6.78, 7.30 (each 2H, d, J=9.0 Hz, aromatic ring proton), 9.66 (1H, s, $H_{20}$).

The compounds of formula (I) show antibacterial activity against both gram-positive and gram-negative bacteria. The following Tables illustrate minimum inhibitory concentrations (MIC's) for a representative sample of the compounds of the invention against gram-positive and gram-negative bacteria as well as bacteria resistant to antibiotics. In the Tables abbreviations with the symbol r attached designate resistant bacterial strains.

EM=erythromycin
TC=tetracycline
PC=penicillin
CP=chloramphenicol
MC=macrolide
KM=kanamycin
SM=streptomycin

TABLE 1

| Bacteria | Antibacterial Activity of Formula (I) Compounds | | | | | | | | | | |
|---|---|---|---|---|---|---|---|---|---|---|---|
| | C | N | O | P | Q | R | S | T | U | V | W |
| *Staphylococcus aureus* ATCC 6538P | 12.5 | 1.56 | 12.5 | 3.12 | 0.78 | 1.56 | 1.56 | 3.12 | 6.25 | 3.12 | 3.12 |
| *Staphylococcus aureus* KB 199(EM$^r$) | >50 | >100 | >100 | >100 | >100 | >100 | 50 | 25 | >100 | 25 | 50 |
| *Bacillus subtilis* PCI 219 | 0.78 | 0.78 | 12.5 | 3.12 | 0.78 | 0.78 | 0.4 | 0.4 | 0.4 | 0.4 | 0.4 |
| *Bacillus cereus* IFO 3001 | 0.78 | 0.78 | 3.12 | 0.78 | 0.2 | 0.78 | 0.4 | 0.4 | 1.56 | 0.4 | 0.4 |
| *Micrococcus luteus* ATCC 9341 | 0.2 | 0.2 | 0.4 | 0.2 | <0.1 | <0.1 | <0.1 | <0.1 | 0.78 | <0.1 | <0.1 |
| *Mycobacterium smegmatis* ATCC 607 | 50 | >100 | >100 | >100 | >100 | 100 | 50 | 50 | >100 | 50 | >100 |
| *Escherichia coli* NIHJ | >100 | >100 | >100 | >100 | 100 | 100 | 100 | 100 | >100 | 100 | 100 |
| *Klebsiella pneumoniae* ATCC 10031 | >100 | 50 | >100 | 100 | 100 | 100 | 100 | 100 | >100 | 100 | 100 |
| *Klebsiella pneumoniae* PCI 602 | >100 | >100 | >100 | >100 | 100 | >100 | 100 | 100 | >100 | 100 | 100 |
| *Salmonella typhirium* KB 20 | >100 | >100 | >100 | >100 | 100 | >100 | 100 | 100 | >100 | 100 | 100 |
| *Proteus vulgaris* IFO 3167 | >100 | >100 | >100 | >100 | 50 | >100 | 100 | 50 | >100 | 50 | 50 |
| *Pseudomonas aeruginosa* P-3 | — | >100 | >100 | >100 | >100 | >100 | >100 | >100 | >100 | >100 | >100 |

TABLE 2

| Antibacterial Activity of Formula (I) Compounds Against Resistant Strains | | | | |
|---|---|---|---|---|
| | Compounds (MIC μg/ml) | | | |
| Resistant Bacteria | S | T | U | W |
| *Staphylococcus aureus* KB 191 (MC, TC$^r$) | 50 | 25 | 25 | 50 |
| *Staphylococcus aureus* KB 219 (MC, TC, PC, CP$^r$) | 100 | 50 | 50 | 100 |
| *Staphylococcus aureus* KB 221 (MC, TC, CP, KM$^r$) | 50 | — | — | — |
| *Staphylococcus aureus* KB 224 (MC, TC, KM, SM$^r$) | 50 | 25 | 25 | 50 |

I claim:
1. A compound of formula (I):

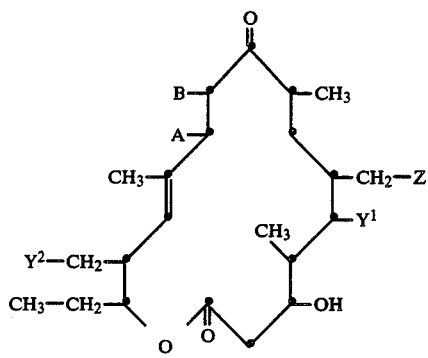 (I)

wherein A represents a group of formula —SR$^1$ where R$^1$ is a C$_{1-6}$ alkyl or C$_{2-6}$ hydroxyalkyl group or a monovalent aryl group when B represents a hydrogen atom;

or A and B taken together represent a single chemical bond;

wherein Y$^1$ represents a group of formula:

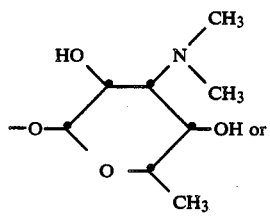

wherein Y$^2$ represents a group of formula:

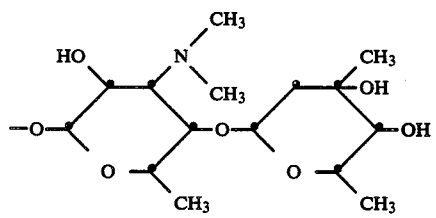

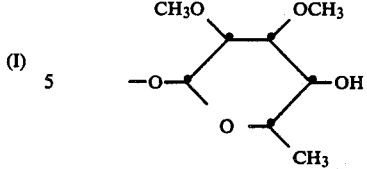

and Z represents CHO or a group of formula

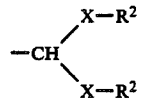

where X represents an oxygen or sulfur atom and R$^2$ is C$_{1-3}$ alkyl or aryl;

provided that, when A and B taken together represent a single chemical bond, then Z cannot be —CHO and X cannot be oxygen;

or a pharmacologically-acceptable salt thereof.

2. A compound of claim 1 in which Z is —CHO, A is —SR$^1$ and R$^1$ is an aryl group.

3. The compound of claim 2 which is 10,11-dihydro-11-(phenylthio)tylosin.

4. The compound of claim 2 which is 11-(p-chlorophenylthio)-10,11-dihydrotylosin.

5. The compound of claim 2 which is 11-(p-aminophenylthio)-10,11-dihydrotylosin.

6. The compound of claim 2 which is 10,11-dihydro-11-(p-methylphenylthio)tylosin.

7. A compound of claim 1 wherein Z is:

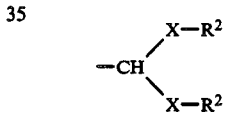

or a pharmacologically-acceptable salt thereof.

8. A compound of claim 7 in which A represents SR$^1$ and B is hydrogen, or a pharmacologically-acceptable salt thereof.

9. A compound of claim 1 in which Z is —CHO, A is SR$^1$ and B is hydrogen.

10. A veterinary formulation which comprises as an active ingredient a compound of claim 1, together with one or more excipients or carriers.

11. A method for treating bacterial infections in warm-blooded mammals which comprises administering to a mammal an amount of a compound of claim 1, which is effective against bacterial infections.

12. A compound of claim 7 wherein A and B taken together represent a single chemical bond or a pharmacologically-acceptable salt thereof.

* * * * *